United States Patent
Majidi et al.

(10) Patent No.: US 10,645,803 B2
(45) Date of Patent: May 5, 2020

(54) SOFT, MULTILAYERED ELECTRONICS FOR WEARABLE DEVICES AND METHODS TO PRODUCE THE SAME

(71) Applicant: CARNEGIE MELLON UNIVERSITY, Pittsburgh, PA (US)

(72) Inventors: Carmel Majidi, Pittsburgh, PA (US); Michael D. Bartlett, Pittsburgh, PA (US); Eric J. Markvicka, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 0 days.

(21) Appl. No.: 16/129,717

(22) Filed: Sep. 12, 2018

(65) Prior Publication Data
US 2019/0082532 A1 Mar. 14, 2019

Related U.S. Application Data (60) Provisional application No. 62/606,182, filed on Sep. 12, 2017.

(51) Int. Cl.
*H05K 1/02* (2006.01)
*H05K 3/00* (2006.01)
(Continued)

(52) U.S. Cl.
CPC .......... *H05K 1/0283* (2013.01); *A61B 5/1123* (2013.01); *A61B 5/6825* (2013.01); *H05K 1/0393* (2013.01); *H05K 1/189* (2013.01); *H05K 3/0032* (2013.01); *H05K 3/303* (2013.01); *A61B 5/6832* (2013.01); *A61B 2562/0261* (2013.01); *A61B 2562/12* (2013.01);
(Continued)

(58) Field of Classification Search
None
See application file for complete search history.

(56) References Cited

U.S. PATENT DOCUMENTS

2014/0275883 A1* 9/2014 Haisley .............. A61B 5/14552
600/324
2015/0099062 A1* 4/2015 Tseng .................... H01M 4/926
427/115
(Continued)

OTHER PUBLICATIONS

Sekitani, T. et al. "A rubberlike stretchable active matrix using elastic conductors." Science 321, No. 5895 (2008): 1468-1472.
(Continued)

*Primary Examiner* — Angel Roman
(74) *Attorney, Agent, or Firm* — Michael G. Monyok (57) ABSTRACT

Disclosed herein is an efficient fabrication approach to create highly customizable wearable electronics through rapid laser machining and adhesion-controlled soft materials assembly. Well-aligned, multi-layered materials can be created from 2D and 3D elements that stretch and bend while seamlessly integrating with rigid components such as microchip integrated circuits (IC), discrete electrical components, and interconnects. These techniques are applied using commercially available materials. These materials and methods enable custom wearable electronics while offering versatility in design and functionality for a variety of bio-monitoring applications.

9 Claims, 8 Drawing Sheets (51) Int. Cl.
  H05K 3/30   (2006.01)
  H05K 1/03   (2006.01)
  H05K 1/18   (2006.01)
  A61B 5/11   (2006.01)
  A61B 5/00   (2006.01)
(52) U.S. Cl.
  CPC .............. H05K 2201/0162 (2013.01); H05K 2201/10151 (2013.01); H05K 2203/107 (2013.01); H05K 2203/166 (2013.01)

(56) References Cited

U.S. PATENT DOCUMENTS

2016/0025669 A1\* 1/2016 Sun .................. H01G 9/022
                                              205/790.5
2016/0100778 A1\* 4/2016 Yi ..................... A61B 5/14532
                                              600/345

OTHER PUBLICATIONS

Hammock, M. et al. "25th anniversary article: the evolution of electronic skin (e-skin): a brief history, design considerations, and recent progress." Advanced materials 25, No. 42 (2013): 5997-6038.
Kim, D-H. et al. "Epidermal electronics." science 333, No. 6044 (2011): 838-843.
Majidi, Carmel. "Soft robotics: a perspective—current trends and prospects for the future." Soft Robotics 1, No. 1 (2014): 5-11.
Pang, C. et al. "A flexible and highly sensitive strain-gauge sensor using reversible interlocking of nanofibres." Nature materials 11, No. 9 (2012): 795.
Rogers, J. et al. "Materials and mechanics for stretchable electronics." science 327, No. 5973 (2010): 1603-1607.
Kaltenbrunner, M. et al. "An ultra-lightweight design for imperceptible plastic electronics." Nature 499, No. 7459 (2013): 458.
Xu, S. et al. "Soft microfluidic assemblies of sensors, circuits, and radios for the skin." Science 344, No. 6179 (2014): 70-74.
Kong, J-H. et al. "Simple and rapid micropatterning of conductive carbon composites and its application to elastic strain sensors." Carbon 77 (2014): 199-207.
Lipomi, D. et al. "Skin-like pressure and strain sensors based on transparent elastic films of carbon nanotubes." Nature nanotechnology 6, No. 12 (2011): 788.
Yao, S. et al. "Nanomaterial-enabled stretchable conductors: strategies, materials and devices." Advanced materials 27, No. 9 (2015): 1480-1511.
Weigel, M. et al. "Iskin: flexible, stretchable and visually customizable on-body touch sensors for mobile computing." In Proceedings of the 33rd Annual ACM Conference on Human Factors in Computing Systems, pp. 2991-3000. ACM, 2015.
Charalambides, A. et al. "A novel all-elastomer MEMS tactile sensor for high dynamic range shear and normal force sensing." Journal of Micromechanics and Microengineering 25, No. 9 (2015): 095009.
Russo, A. et al. "Pen-on-paper flexible electronics." Advanced materials 23, No. 30 (2011): 3426-3430.
Yokota, T. et al. "Ultraflexible organic photonic skin." Science advances 2, No. 4 (2016): e1501856.
Schwartz, G. et al. "Flexible polymer transistors with high pressure sensitivity for application in electronic skin and health monitoring." Nature communications 4 (2013): 1859.
Muth, J. et al. "Embedded 3D printing of strain sensors within highly stretchable elastomers." Advanced Materials 26, No. 36 (2014): 6307-6312.
Park, Y-L. et al."Hyperelastic pressure sensing with a liquid-embedded elastomer." Journal of Micromechanics and Microengineering 20, No. 12 (2010): 125029.
Microfluidic, A. "Reversibly Stretchable, Large-Area Wireless Strain Sensor Cheng, Shi; Wu, Zhigang." Advanced Functional Materials 21, No. 12 (2011): 2282-2290.
Chossat, J-B. et al. "Wearable soft artificial skin for hand motion detection with embedded microfluidic strain sensing." In Robotics and Automation (ICRA), 2015 IEEE International Conference on, pp. 2568-2573. IEEE, 2015.
Sun, J-Y. et al. "Ionic skin." Advanced Materials 26, No. 45 (2014): 7608-7614.
Hughes, D. et al. "A soft, amorphous skin that can sense and localize textures." In Robotics and Automation (ICRA), 2014 IEEE International Conference on, pp. 1844-1851. IEEE, 2014.
Gomez, C. et al. "Overview and evaluation of bluetooth low energy: An emerging low-power wireless technology." Sensors 12, No. 9 (2012): 11734-11753.
Yu, B. et al. "Bluetooth Low Energy (BLE) based mobile electrocardiogram monitoring system." In Information and Automation (ICIA), 2012 International Conference on, pp. 763-767. IEEE, 2012.
McEvoy, M. et al. "Materials that couple sensing, actuation, computation, and communication." Science 347, No. 6228 (2015): 1261689.
Liu. C-X. et al "Embedding conductive patterns of elastomer nanocomposite with the assist of laser ablation." . Microsystem technologies 18, No. 3 (2012): 365-371.
Chuang, H-S. et al. "Rapid patterning of slurry-like elastomer composites using a laser-cut tape." Journal of Micromechanics and Microengineering 19, No. 9 (2009): 097001.
Lu, T. et al. "Rapid Prototyping for Soft-Matter Electronics." Advanced Functional Materials 24, No. 22 (2014): 3351-3356.
Lipson, H. et al. "Fabricated: The new world of 3D printing." John Wiley & Sons, 2013.
Dulpepper, Martin L. "Design of quasi-kinematic couplings." Precision Engineering 28, No. 3 (2004): 338-357.
Childs, W. et al. "Decal transfer microlithography: a new soft-lithographic patterning method." Journal of the American Chemical Society 124, No. 45 (2002): 13583-13596.
Meitl, Ma. et al. "Transfer printing by kinetic control of adhesion to an elastomeric stamp." Nature materials 5, No. 1 (2006): 33.
Ghatak, A. et al. "Interfacial rate processes in adhesion and friction." (2000): 4018-4030.
Wang, X. et al. "Silk-molded flexible, ultrasensitive, and highly stable electronic skin for monitoring human physiological signals." Advanced materials 26, No. 9 (2014): 1336-1342.
Bartlett, M. et al. "Scaling normal adhesion force capacity with a generalized parameter." Langmuir 29, No. 35 (2013): 11022-11027.
Bartlett, M. et al. "Material transfer controlled by elastomeric layer thickness." Materials Horizons 1, No. 5 (2014): 507-512.
Rowell, L. et al. "Saturation of arterial blood with oxygen during maximal exercise." Journal of applied physiology 19, No. 2 (1964): 284-286.
Slocum, Alexander. "Kinematic couplings: A review of design principles and applications." International journal of machine tools and manufacture 50, No. 4 (2010): 310-327.
Wukitsch, M. et al. "Pulse oximetry: analysis of theory, technology, and practice." Journal of clinical monitoring 4, No. 4 (1988): 290-301.
Goldman, J. et al. "Masimo signal extraction pulse oximetry." Journal of clinical monitoring and computing 16, No. 7 (2000): 475-483.

\* cited by examiner

SOFT, MULTILAYERED ELECTRONICS FOR WEARABLE DEVICES AND METHODS TO PRODUCE THE SAME

CROSS-REFERENCE TO RELATED APPLICATIONS

This application claims the benefit under 35 U.S.C. § 119 of Provisional Application Ser. No. 62/606,182, filed Sep. 12, 2017, which is incorporated herein by reference.

STATEMENT REGARDING FEDERALLY SPONSORED RESEARCH

This invention was made with government support under NASA No. NNX14AO49G. The government has certain rights in this invention.

BACKGROUND OF THE INVENTION

Progress in the performance, multi-functionality, and accessibility of soft electronic materials has allowed for wearable devices with reduced dependency on rigid or inextensible printed circuit boards. These advances have led to the emergence of deformable circuits and sensors that avoid mechanical incompatibility with skin by matching the elastic properties of soft biological tissue. Applications include wearable monitoring of physiological signals, electronic skin for data entry, and skin-mounted sensors for joint proprioception and motion capture. The ability for these electronics to bend, twist, and stretch is accomplished by using soft elastomers as a carrier medium for deterministically-patterned metal wiring, percolating networks of conductive nanoparticles, grafted electrically active ionomers and conductive polymer groups, and conductive fluids such as carbon filled grease, liquid metals, and ionic liquids. While promising, efforts to incorporate these materials into fully-integrated wearable devices are currently limited by the lack of robust and size-scalable rapid prototyping techniques. Current fabrication methods typically require customized equipment or clean-room fabrication, can be labor-intensive, and take hours to days to create fully functional devices. Such constraints can limit personalized configurations and slow down design iterations, which can be particularly limiting in creating devices for multiple users. These various drawbacks make it difficult to accelerate development and can be potential barriers for scalability and commercialization, especially in the emerging area of personalized health monitoring.

Robust integration of soft materials into wearable computing and bio-monitoring systems requires a comprehensive fabrication approach that allows for a broad range of electronic materials, substrates, circuit architectures, and surface-mounted technologies. This includes reliable methods for patterning, precision alignment, bonding, encapsulation, and electrical interfacing. The latter is particularly essential for local computation and communication, energy-efficient wireless networks, and connectivity with external hardware for power or signal processing. Advances in rapid prototyping techniques such as 3D printing and laser machining of soft materials provide paths forward to achieve these objectives while accelerating design cycles and commercial development. Recent work has shown how these approaches can enable the fabrication of multiple sensors at once with soft materials. However, methods like 3D printing are limited in the mechanical and electrical performance of their build materials and do not support automated integration of IC components, which are necessary for fast, energy efficient, and miniaturized signal processing and communication. This is especially limiting for applications in wearable physiological sensing and bio-monitoring that rely on packaged microchips for biosignal acquisition and processing. Salient examples of this include photoplethysmography (PPG), peripheral capillary oxygen saturation ($SpO_2$) detection, and other modalities that involve optical biosensing. Therefore, a key challenge in wearable bio-monitoring remains the complete and sequential integration of soft sensors, stretchable electrical interconnects, and miniaturized hardware for communication, power, and signal processing through scalable techniques for patterning, encapsulation, bonding, and attachment to soft carrier films.

BRIEF SUMMARY

Described herein are robust fully functional, skin-mountable electronic devices and methods for producing the same. These devices are fabricated using rapid prototyping and assembly techniques that integrate multiple soft material layers, for example soft non-tacky elastomers, and rigid elements in a single process. In one example embodiment, the fabrication method comprises using a readily available $CO_2$ laser outfitted with a simple alignment system to allow for the precise assembly of sensors through deterministic, adhesion-controlled soft transfer printing techniques. Assembly of the patterned material is controlled by modifying either the adhesion energy of a soft substrate or by adjusting the laser processing conditions. The sensors do not require curing, surface modification, or additional chemical reactions and are bonded together through the inherent adhesion of the soft layers. This enables rapid fabrication that is not dependent on cure kinetics. In other embodiments, the fabrication technique is extended to a UV laser system, which expands the choice of allowable materials (including thin metal film) and enables the rapid fabrication of custom stretchable electronics through deterministic architectures.

DETAILED DESCRIPTION

Figure 1:
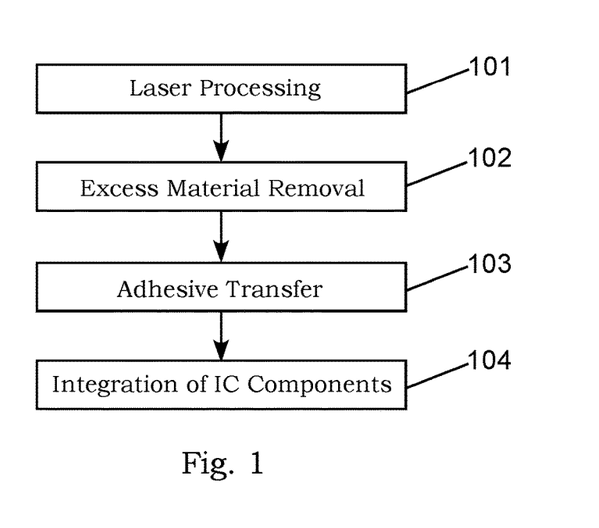
FIG. 1 is a flowchart of the method of the present invention, according to one embodiment.

The rapid fabrication of soft functional materials of the present invention uses a combination of laser cutting with alignment control to create layers of a multilayered device and assembly of the layers through the deployment of a soft transfer printing technique. Referring to the flowchart depicted in FIG. 1, the method of fabrication comprises laser processing (step 101), removal of excess material (step 102), adhesive transfer (step 103), and integration of integrated circuit (IC) components (step 104).

Figure 2:
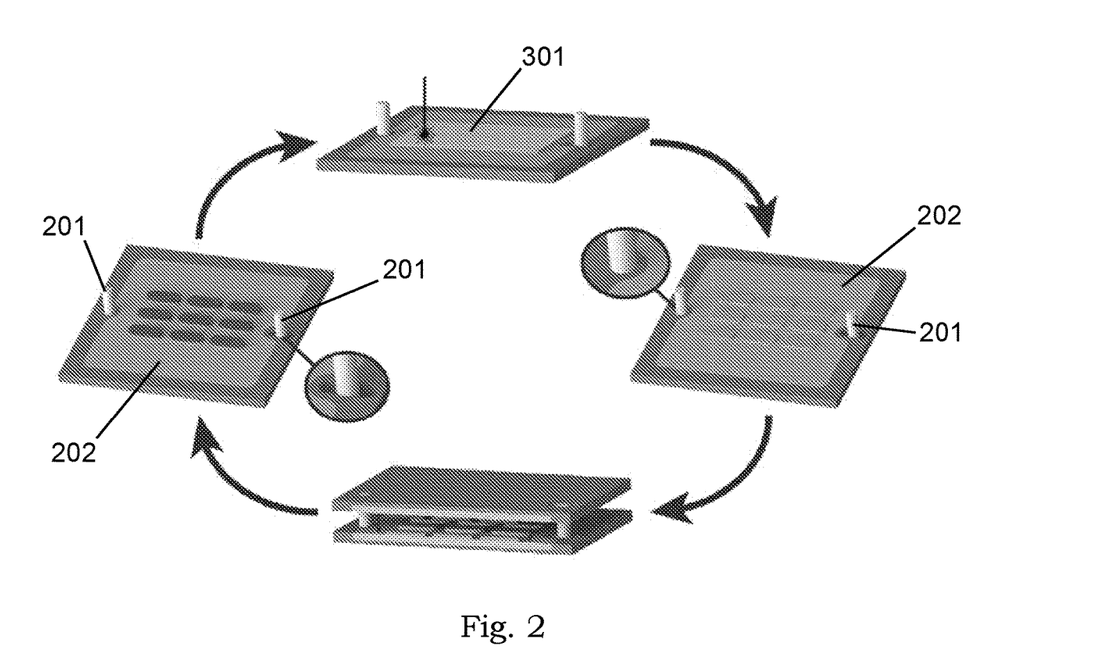
FIG. 2 is a diagram depicting the fabrication process of a multilayer device.

As shown in FIG. 2, laser processing in step 101 involves cutting and patterning a material 301 that will form a layer of the multilayer device 300. A single layer can be laminated to a substrate 202 and patterned, or multiple layers can be laminated and patterned during a single cutting operation. In one embodiment, the materials have the following characteristics: i) low effective elastic modulus, ii) high extensibility, iii) processable by laser cutting, and iv) bonding compatibility. However, other characteristics of the material may vary depending on the device 300 being fabricated. For example, in one embodiment, materials satisfying these criteria can include off-the shelf materials such as insulating or dielectric (VHB 4905, 3M) and conducting (eCAP 7805, 3M) acrylic tapes. These materials are soft, highly extensible, and, due to their inherent bonding characteristics, provide robust adhesion upon lamination under light pressure without additional treatment. Additionally, these materials are readily available in roll form and thus offer the advantage of being easily accessible, available in large quantities, and amenable to scalable production.

Referring again to FIG. 2, a soft substrate 202, or stamp, is used to support the material 301 during processing. The substrate 202 may further comprise a supporting backing, such as a metal plate, with a machined hole and a slot used as part of a locating mechanism 201. With the locating mechanism 201, the substrate 202 can be precisely positioned during each step of the fabrication process. The substrate 202 serves as a base for cutting and assembling layers of the multilayer device 300. The soft substrates can be non-tacky elastomers, such as silicone or soft polyurethanes, such as polydimethylsiloxane (PDMS).

After laser cutting, excess material is removed from the substrate 202 at step 102. At this stage, the material remaining on the substrate 202 is material that will form a layer in the multilayer device 300. Steps 101 and 102 can be repeated on separate substrates 202 to create additional layers that can be joined to form the device. Once the patterning for all layers is complete, at step 103 the individual layers are assembled through the deterministic soft material transfer printing process. During this step, the patterned layer or layers on a first substrate 202 is brought into contact with the patterned layer laminated to a second substrate 202. When the substrates 202 are separated, the layers of material 301 will remain in contact, with one layer being delaminated from its substrate 202. The force of adhesion between the combined layers is stronger than the force of adhesion between the delaminated layer and its substrate, resulting in the transfer of the layer from its substrate. Additional layers can be added to the first combined layers using the same process. After layers are transferred, at step 104 IC components are integrated, if necessary for the device 300. Depending on the intended use, the layers and IC components can be encapsulated to protect the device 300.

Referring again to FIG. 2, the locating mechanism 201 comprises a hole machined into the backing of the substrate 202 and a complimentary pin disposed on the fixture 203, assembly table, or other structure used during fabrication. While a hole and pin are disclosed in this example embodiment, other mechanical interfaces such as slot, peg, recess, or similar structures can be used to align and position the substrate 202. The locating mechanism 201 provides low-cost, kinematically-constrained alignment with sub-millimeter precision.

Figure 3:
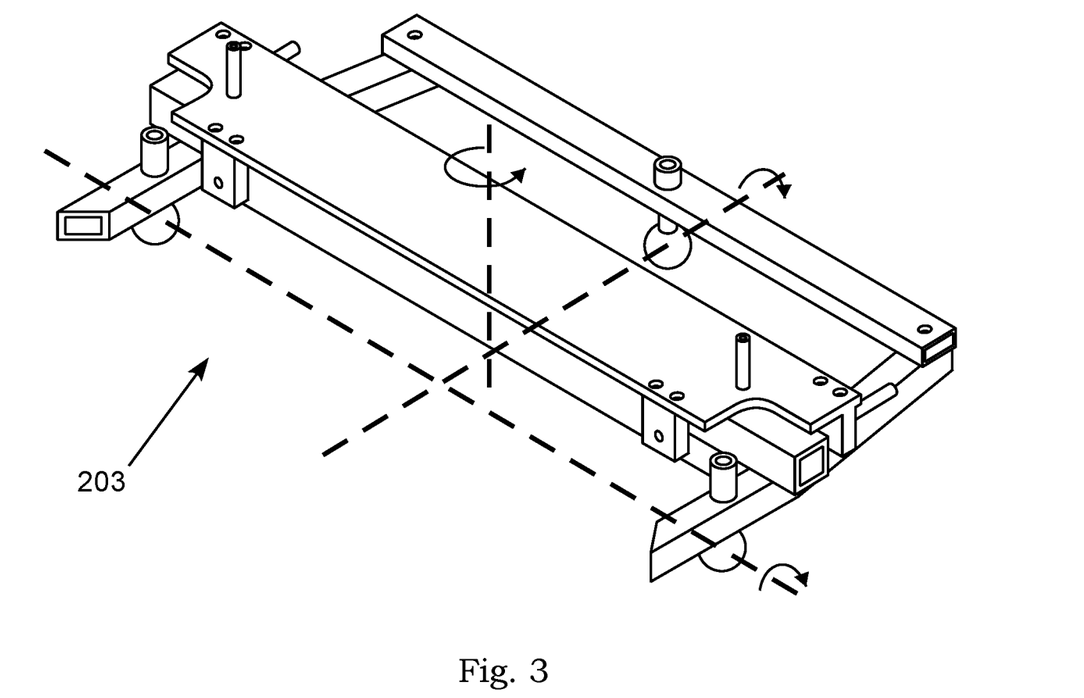
FIG. 3 depicts an alignment fixture.

To further control alignment during cutting, the substrate can be mounted to an alignment fixture 203, which is capable of being placed into a laser cutter (for example, a 30 Watt VLS3.50 $CO_2$ laser cutter; Universal Laser Systems). As shown in FIG. 3, the fixture 203 has 6 degrees of freedom (DOF) to provide corrections in orientation for uniform cutting conditions across a substrate and repeatable alignment within the laser in XYZ for subsequent substrates 202.

As an example of the type of devices 300 that can be fabricated using this method, a batch of 108 cm-scale strain sensors were created in under 45 minutes with 100% yield. Electrical characterization reveals that the sensors are nearly identical, with an average value of 7.6±0.1 pF across the array of sensors, a difference of less than 2%. The strain sensor device 300 comprises two layers of conducting material separated by an insulating layer, with an insulating layer on the exterior of each side.

In this example embodiment, the process of fabricating the strain sensor begins at step 101 using a 30 Watt $CO_2$ laser system outfitted with an alignment fixture 203 (see FIG. 3) supporting PDMS (Dow Corning Sylgard 184) substrates 202 for laser machining. The PDMS substrates 202 are mixed at oligomer to curing agent ratios of 5:1, 10:1, 20:1, and 30:1 and are cured at room temperature on a flat, level surface for 48 hours and then post cured in an oven at 70 C for four hours. The materials 301 used for the sensor 300, comprising conducting and insulating tapes, are laminated onto the PDMS substrates 202 and then laser cut with a predefined pattern. After laser cutting, at step 102 excess material is stripped off and any release liners are removed by cleaning the surface with isopropyl alcohol and then adhesive tape is used to remove all release liners simultaneously. Alternative processes may be used to release the liners. Layers are then assembled on alignment pegs which interface with a hole and slot in each of the substrates 202. A first layer contains an insulating material and conductive material laminated to a 5:1 mixing ratio substrate 202. A second layers contains an insulating layer laminated to a 5:1 mixing ratio substrate 202. A third layer contains an conductive material and insulating material laminated to a 30:1 mixing ratio substrate 202. At step 103, pressure is applied with a roller to ensure adhesive contact between layers and then the upper substrate 202 is peeled off to transfer the patterned elements, creating a five layer electronic device 300. The sensors 300 in this example were 18+/−1 mm long, 6.5 mm wide, and 1.8 mm thick.

Figure 4:
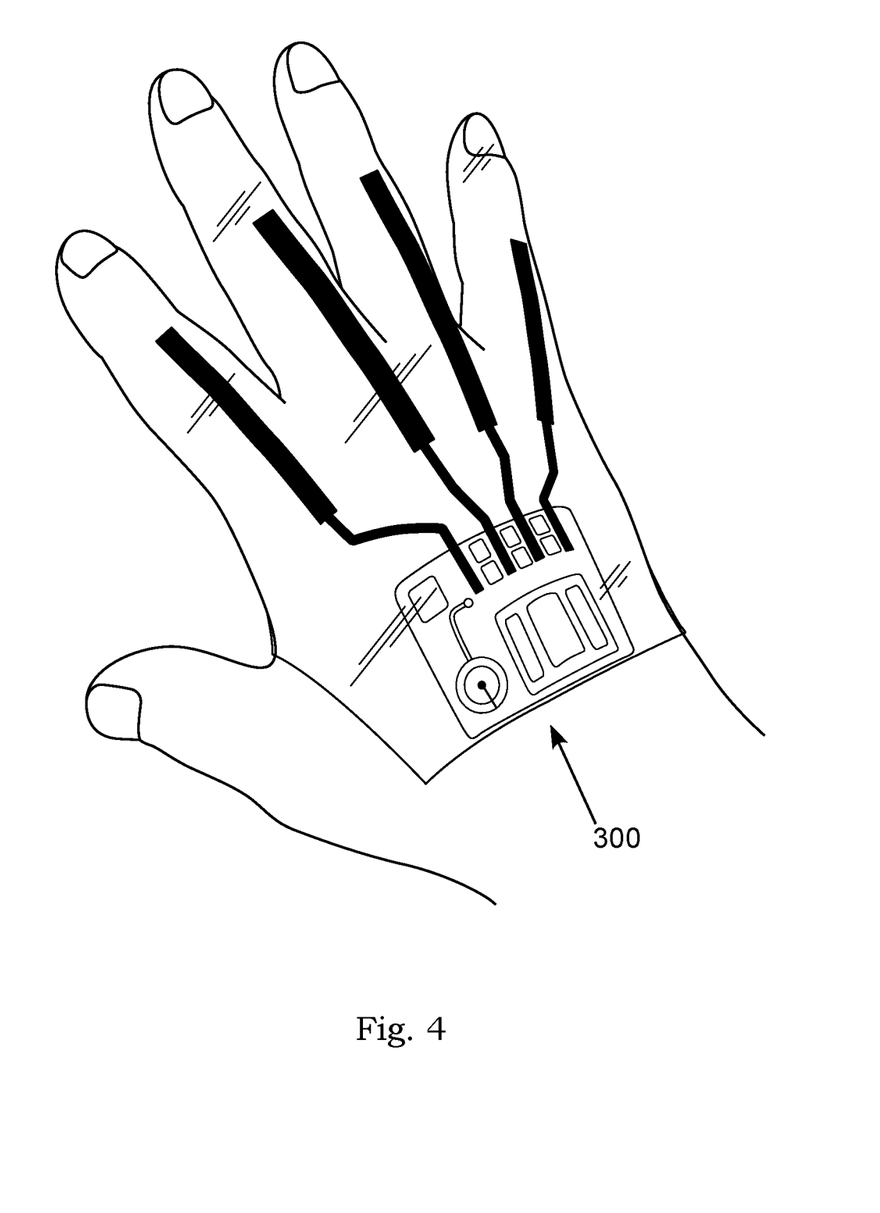
FIG. 4 shows an integrated multilayer device fabricated by the method of the present invention.

In another example embodiment, integrated skin sensors 300 are fabricated using the method of the present invention. Body mounted electronics that are designed to naturally interface with the human skin can provide inherent advantages and superior sensitivity for health monitoring compared to devices made from rigid materials. The device 300 comprises a customizable integrated sensor that adheres to the hand and monitors hand gestures, as shown in FIG. 4. The device 300 contains four capacitive strain sensors that extend over the metacarpophalangeal and proximal interphalangeal joints of each finger. Stretchable circuit interconnects are used to connect the sensor elements to a flexible printed circuit (FPC) board that contains a Bluetooth transceiver and is powered with a coin cell battery. The interconnects are composed of laser-patterned eCAP 7805 conductive tape, which bonds to the terminals of the FPC. The fabrication of the soft integrated skin sensor follows the methodology above with the added capability of transferring the FPC interface board onto the integrated sensor during the processing to ensure proper alignment. The integrated skin sensor adheres to the hand using a medical grade, highly breathable adhesive dressing (Tegaderm, 3M). The wearable system is lightweight (less than 5 grams) and thin enough to fit under an examination glove.

Figure 5A:
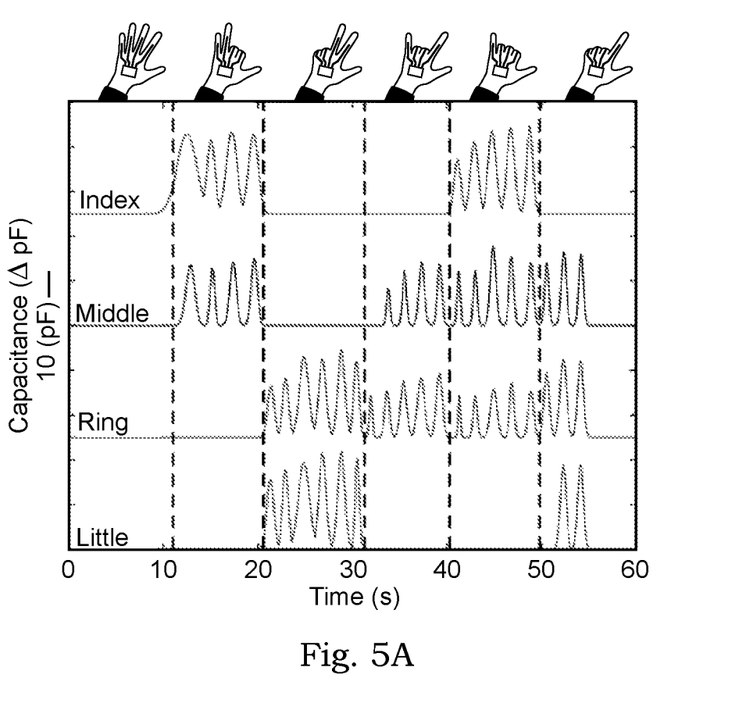
FIGS. 5A-5B are graphs depicting the signals generated by an integrated skin sensor fabricated by the method of the present invention.
Figure 5B:
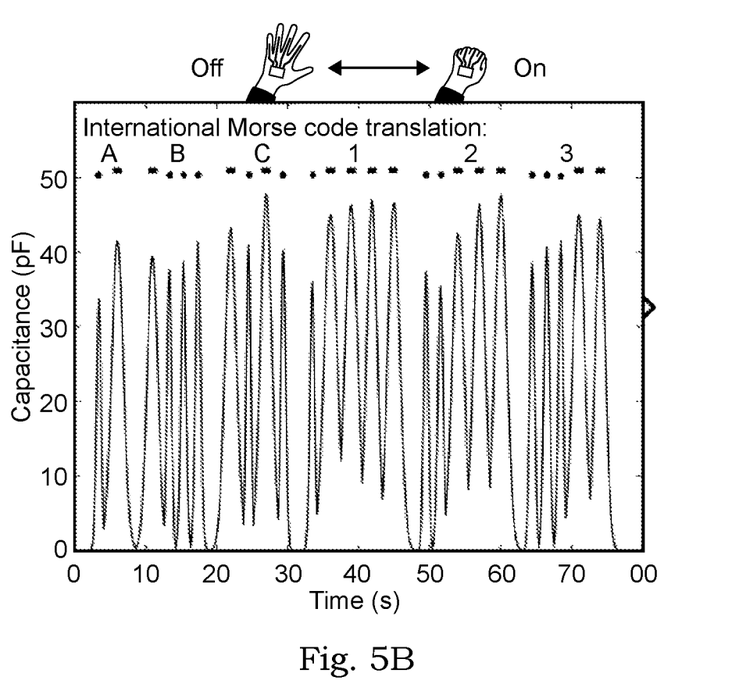

The functionality of the integrated skin is shown by a series of hand gestures. As seen in FIG. 5A, a variety of gestures are recognized by the integrated skin sensor 300. In these experiments, the hand cycles through different multi-finger gestures, where capacitance of the individual strain sensors is measured. Further, alpha-numeric data communication is also possible through the integrated sensing skin, where Morse code can be generated by opening and closing the hand at different frequencies to generate the three communication states: dot, dash, and silence. This is demonstrated in FIG. 5B, where A-B-C-1-2-3 is transmitted and is interpreted through software to automatically identify the pattern of dots and dashes.

Figure 6A:
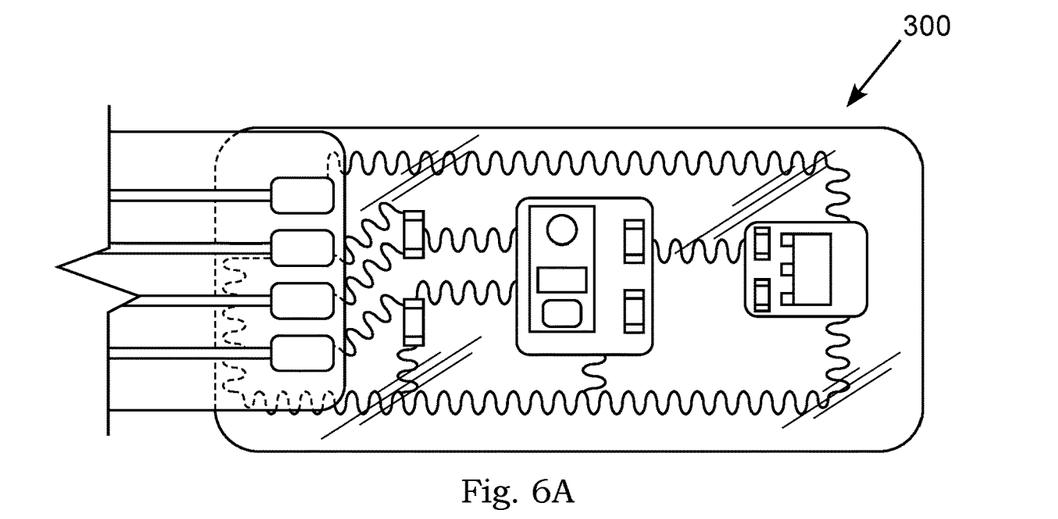
FIGS. 6A-6C depict a multilayer device fabricated by an alternative embodiment of the method of the present invention.

In yet another example embodiment, skin mountable pulse oximeter devices 300 are fabricated. To extend this fabrication methodology to a wider variety of materials, in this embodiment a UV laser micromachining system (ProtoLaser U3; LPKF) is used in step 101. A UV laser system is capable of patterning metals in addition to polymeric materials. Instead of an alignment fixture 203, the laser micromachining system is equipped with a fiducial recognition camera. Material assembly follows the same principals as the $CO_2$ laser fabrication, where an alignment mechanism 201 (i.e. pegs) control layer alignment and deterministic adhesion transfer printing assembles each layer into a multilayer construction. This process takes advantage of the additional material capabilities by laser patterning serpentine architectures of stretchable interconnects out of 70 µm thick flexible copper-clad laminated composite (FR7031 DuPont) to create a wearable pulse oximeter (FIG. 6A). This soft device is capable of bending and stretching (FIG. 6B) and consists of a combination of soft materials and rigid components (FIG. 6C) which are all sequentially assembled through the laser patterning and adhesion assembly process.

Figure 6B:
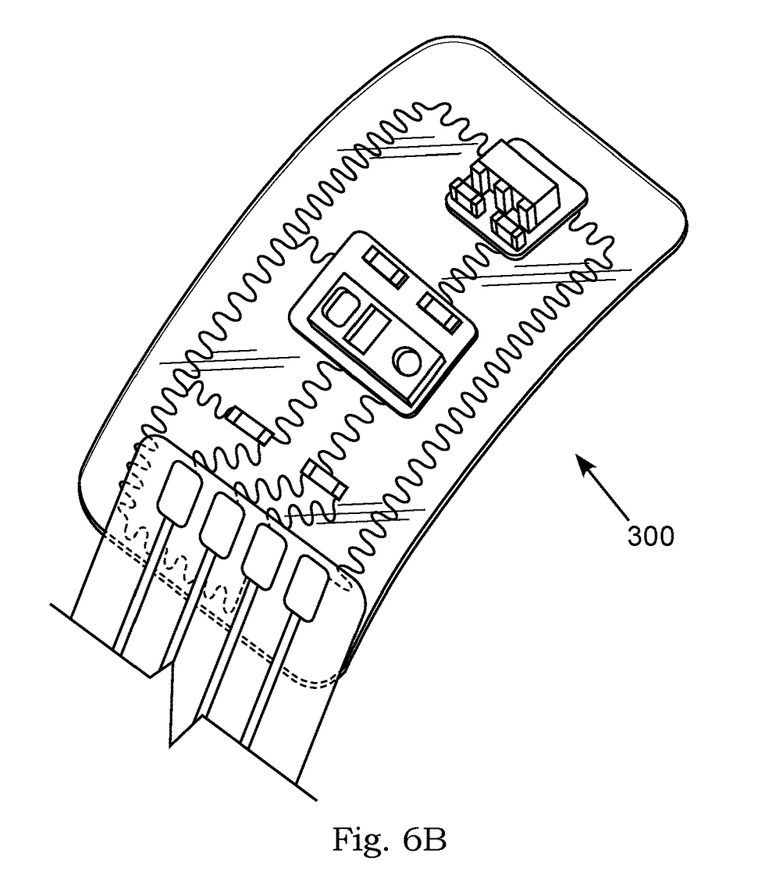
Figure 6C:
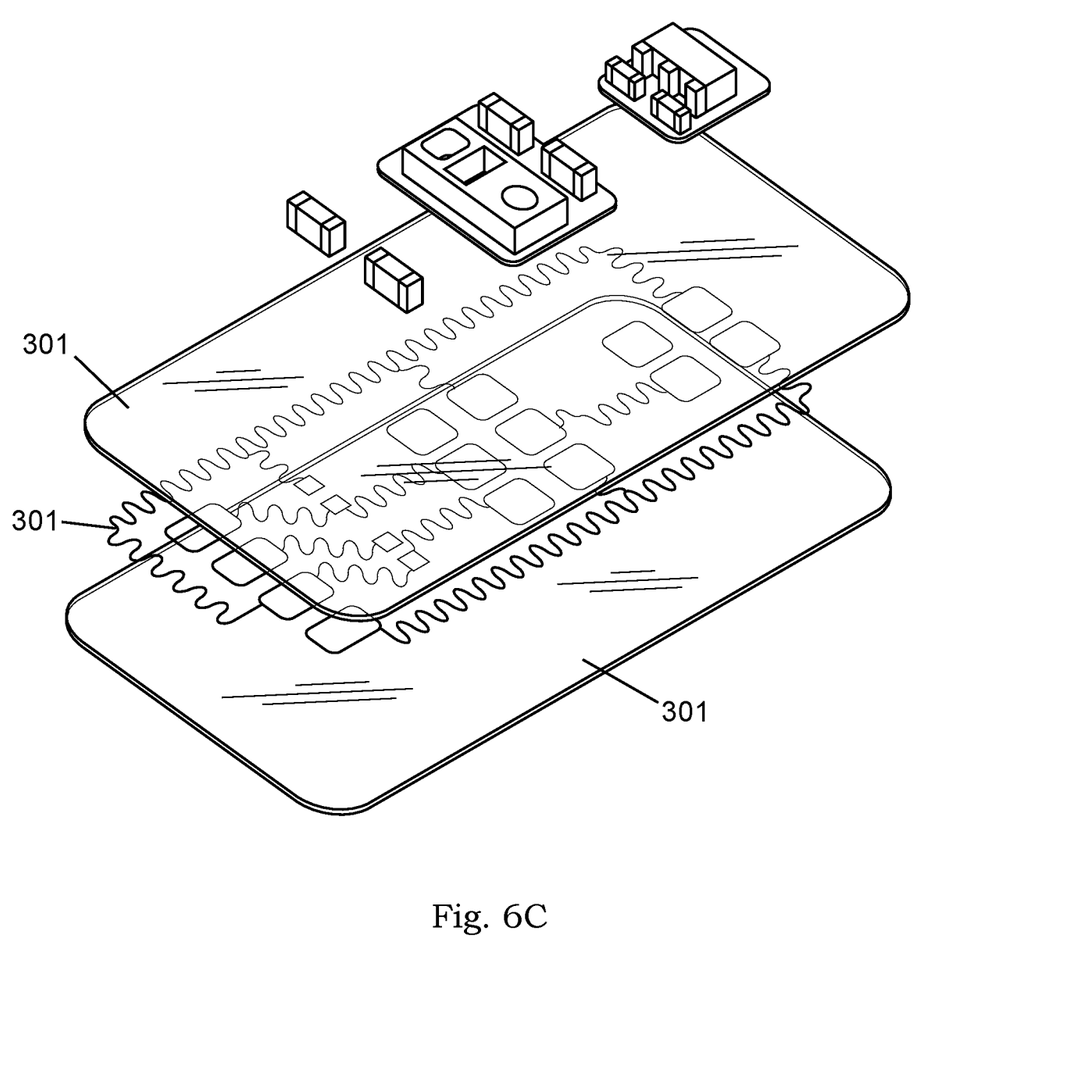

During assembly of the rigid components the PDMS substrate 202 thickness was chosen so that the lateral dimension of the rigid component was no more than twice the substrate thickness to avoid adhesion effects from substrate confinement. The multilayer composite consists of a medical grade adhesive for bonding to the skin, laser patterned flexible copper-clad interconnects, a thru thickness conductive adhesive layer (ECATT 9703; 3M) which serves to electrically and adhesive connect the interconnects to the active and passive electrical components and prevent shorting within the plane in the pulse oximeter circuit. The parallel processing capabilities of the assembly process allows simultaneous assembly of four, fully functional wearable pulse oximeter devices. The ability to assemble planar as well as three dimensional components of both soft and rigid elements in a parallel manner provides versatility to create a variety of functional wearable devices.

Figure 7:
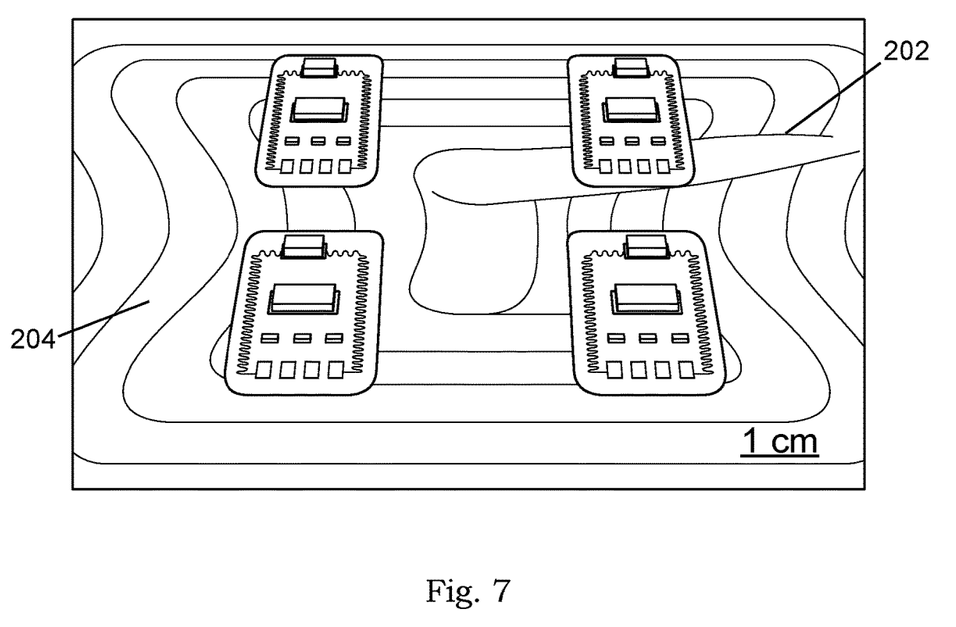
FIG. 7 shows multiple multilayer devices on a substrate.

In this example embodiment, a LPKF ProtoLaser U3 UV laser micromachining system was used with camera based fiducial recognition to automatically and reliably locate the position of PDMS substrates 202 that have fiducials 204 machined into the substrate (see FIG. 7). The fiducials 204 are precisely placed relative to the hole and slot that is used for alignment during the adhesive transfer process. PDMS is mixed at oligomer to curing agent ratios of 5:1, 10:1, and 20:1 and are cured at room temperature on a flat, level surface for 48 hours and then post cured in an oven at 70 C for four hours. Interconnect material is laminated onto the PDMS substrates 202, the fiducials are automatically located, and the material is laser cut with a predefined pattern. After laser cutting, excess material is stripped off and any release liners are removed. Individual stencils were patterned out of release liner for the transfer of the rigid electrical components. Layers are then assembled on alignment pegs which interfaces with a hole and slot in the substrate 202. A first layer includes a component stencil and a stacked release liner on a 5:1 mixing ratio substrate 202. A second layer consists of a Z-film on a 10:1 mixing ratio substrate 202. A third layer includes the copper-clad laminated composite on a 10:1 mixing ratio substrate 202. A fourth layer includes a transparent film adapted for contact with human skin (Tegaderm) on a 20:1 mixing ratio substrate 202. Pressure is applied to the top substrate 202 to ensure adhesive contact between layers and then the upper substrate 202 is peeled off to transfer the patterned elements.

When several layers are used, the assembly of both rigid and soft components through an adhesion-based, transfer printing process is challenging due to the varying material stiffness, viscoelastic response, and interfacial properties. Previous work with transfer printing soft elastomer layers includes decal transfer lithography, which involves chemical bonding treatments and multiple steps to transfer a single layer. Kinetic controlled transfer printing can be used without chemical treatments but relies on rate dependent adhesion, which can be challenging with multiple rate dependent components in the system. To overcome these challenges, the material assembly in the present invention at step 103 is accomplished by controlling the substrate 202 adhesion energy by modifying their viscoelastic response through mixing ratio and by using laser cutting to tune adhesion response. By altering the mixing ratio of the PDMS material, for example, the modulus of elasticity of the cured substrate 202 can be controlled. This enables deterministic material construction in multi-dimensional layouts.

Figure 8A:
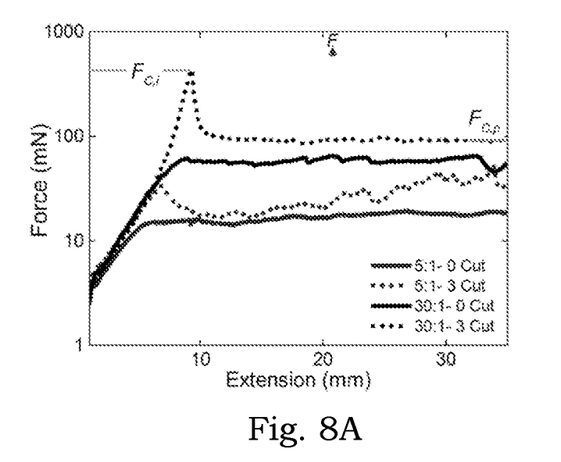
FIGS. 8A-8C are graphs showing the peeling force.

To characterize the adhesion transfer process of step 103, 90° peel experiments can be conducted. The samples are prepared in the same manner as the transfer process and after removing excess sensor material, an inextensible film is adhered to the sensor and then loaded into a peel setup. Representative peel adhesion curves for 5:1 and 30:1 substrates are presented in FIG. 8, where the force increases until crack initiation, $F_{c,i}$, and then drops as the crack begins to propagate at a constant force, $F_{c,p}$. Both the substrate 202 choice and laser cutting conditions control the adhesion behavior. It should be noted that the y-axis in FIG. 8 is plotted on a log scale to capture the significant differences in adhesion force for the different conditions. Specifically, after three laser cuts the 30:1 substrate has an initiation force which is over 10× higher than the 5:1 substrate. This difference enables the samples to be controllably transferred from the 5:1 substrate to the 30:1 substrate, since the sample will separate from the 5:1 substrate before the other sample will separate from the 30:1 substrate.

Figure 8B:
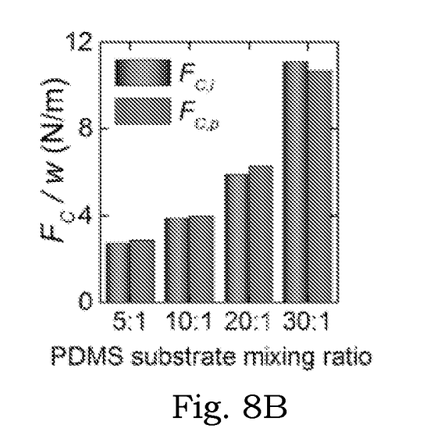
Figure 8C:
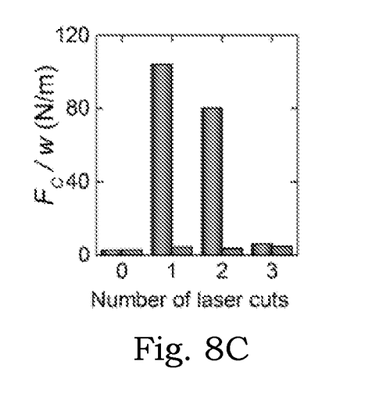

Adhesion control can be investigated further by varying the substrate mixing ratio from 5:1 to 30:1 and varying the laser cutting from 0 to 4 passes on the same location on the substrate 202. For the case where sensors are laminated onto the substrates with no laser cutting, there is an increase in peel adhesion force as the mixing ratio of the substrates increases (FIG. 8B). This can be attributed to the increasing viscoelastic response of the materials as the mixing ratio increases due to greater dissipation near the crack tip. As a result, laser cutting can also act as a control parameter in this transfer process. For example, as seen in FIG. 8C, the peel initiation force increases by nearly 40× when a sensor is laser cut on the 5:1 substrate compared to just laminating the sensor onto the substrate. As subsequent cuts are made this initiation force decreases and on the third pass the force nearly returns to the laminated value.

As the sensor layers become impinged into the PDMS substrate 202 upon laser cutting, a greater force is required to separate the materials at the contact edge. This effect is reduced upon subsequent cutting as the already formed cut line in the PDMS substrate 202 reduces the interaction between the sensor layers and the substrate 202. This result allows the substrates 202 to be used over many fabrication cycles, because the laser cutting effects diminish upon subsequent cutting and the substrate adhesion energy then dominates the transfer process at step 103. The stamp 202 can also be preconditioned by running the laser cutter over the stamp at a reduced power and speed before the material is laminated to the stamp to diminish the impinging effect of laser cutting.

The rapid assembly process for soft multilayered electronics presented here is efficient, highly customizable, and employs materials and equipment that are readily accessible. This method was demonstrated on two different laser micromachining systems at the sub-mm to cm scale. More than ten different materials (IC components, discrete circuit elements, soft insulators, and conductive soft adhesive films) are transferred using a deterministic adhesive-transfer approach. This versatility in fabrication and materials selection allows for varying shapes (2D/3D), sizes (0.01 to 100 $cm^2$), and materials properties (Young's modulus from ~100 kPa to 100 GPa). Adhesion-controlled transfer was influenced by the choice of substrate (peel initiation force increases greater than 10×) and laser cutting conditions (peel initiation force increases by nearly 40×).

What is claimed is:

1. A method of fabricating a wearable electronic device comprising:
    affixing a material to a first substrate;
    patterning the material with a laser cutter;
    removing excess material from the first substrate to create a first layer;
    creating at least one additional layer on an additional substrate,
        wherein a force of adhesion between the first substrate and the first layer is not equal to a force of adhesion between the additional substrate adhesion and the at least one additional layer;
    contacting the first layer and the at least one additional layer,
        wherein the first layer releases from the first substrate or the at least one additional layer releases from the additional substrate upon contact; and
    integrating an IC component.

2. The method of claim 1, wherein at least one of the first substrate and the additional substrate comprises polydimethylsiloxane.

3. The method of claim 2, further comprising:
    adjusting the modulus of elasticity of at least one of the first substrate and the additional substrate to affect its adhesion.

4. The method of claim 1, further comprising:
    patterning at least one of the first substrate and the additional substrate to affect its adhesion.

5. The method of claim 1, wherein the material is an acrylic tape.

6. The method of claim 1, wherein joining the first layer and the at least one additional layer comprises:
    aligning the first substrate of the first layer and the additional substrate of the at least one additional layer with a locating mechanism.

7. The method of claim 6, wherein the locating mechanism comprises a slot on each of the first substrate and the additional substrate and a pin.

8. A soft multilayer electronic device comprising:
    a first layer of material patterned in a laser cutter and affixed to a first substrate;
    at least one additional layer of material patterned in the laser cutter, wherein the at least one additional layer of material is affixed to the first layer via adhesion,
        wherein the at least one additional layer is transferred from a second sub state,
        wherein the second substrate has a lower adhesion energy than the first substrate.

9. The soft multilayer device of claim 8, wherein the first layer of material is a dielectric tape and the at least one additional layer is a conductive tape.

* * * * *